United States Patent
Kawamura

Patent Number: 5,171,440
Date of Patent: Dec. 15, 1992

[54] COLUMN FOR LIQUID CHROMATOGRAPHY

[75] Inventor: Katsumi Kawamura, Tokyo, Japan

[73] Assignee: Asahi Kogaku Kogyo K.K., Tokyo, Japan

[21] Appl. No.: 734,114

[22] Filed: Jul. 24, 1991

Related U.S. Application Data

[63] Continuation of Ser. No. 449,399, Dec. 13, 1989, abandoned, which is a continuation of Ser. No. 246,368, Sep. 19, 1988, abandoned.

[30] Foreign Application Priority Data

Sep. 17, 1987 [JP]  Japan ................. 62-233327

[51] Int. Cl.⁵ .................................. B01D 15/08
[52] U.S. Cl. .................... 210/198.2; 210/502.1; 210/510.1; 210/656; 55/386
[58] Field of Search ............ 210/635, 656, 198.2, 210/509, 502.1, 510.1; 502/8, 208, 400; 423/308; 55/386

[56] References Cited

U.S. PATENT DOCUMENTS

| 4,097,935 | 7/1978 | Jarcho | 423/625 |
| 4,503,157 | 3/1985 | Hatahira | 264/60 |
| 4,636,316 | 1/1987 | Harris | 210/656 |
| 4,655,917 | 4/1987 | Shackelford | 210/198.2 |
| 4,708,654 | 11/1987 | Fujiu | 501/1 |
| 4,711,769 | 12/1987 | Inoue | 423/308 |

FOREIGN PATENT DOCUMENTS 62-206445  9/1987  Japan ................. 210/198.2

*Primary Examiner*—Ernest G. Therkorn
*Attorney, Agent, or Firm*—Sughrue, Mion, Zinn, Macpeak & Seas

[57] ABSTRACT

A column for liquid chromatography comprising particles of a calcium phosphate based compound packed in a column, wherein particles of a calcium phosphate based compound which are packed in the portion of said column where a solvent is to be injected have a durability higher than that of particles of a calcium phosphate compound which are packed in the remaining portion of said column.

6 Claims, 3 Drawing Sheets

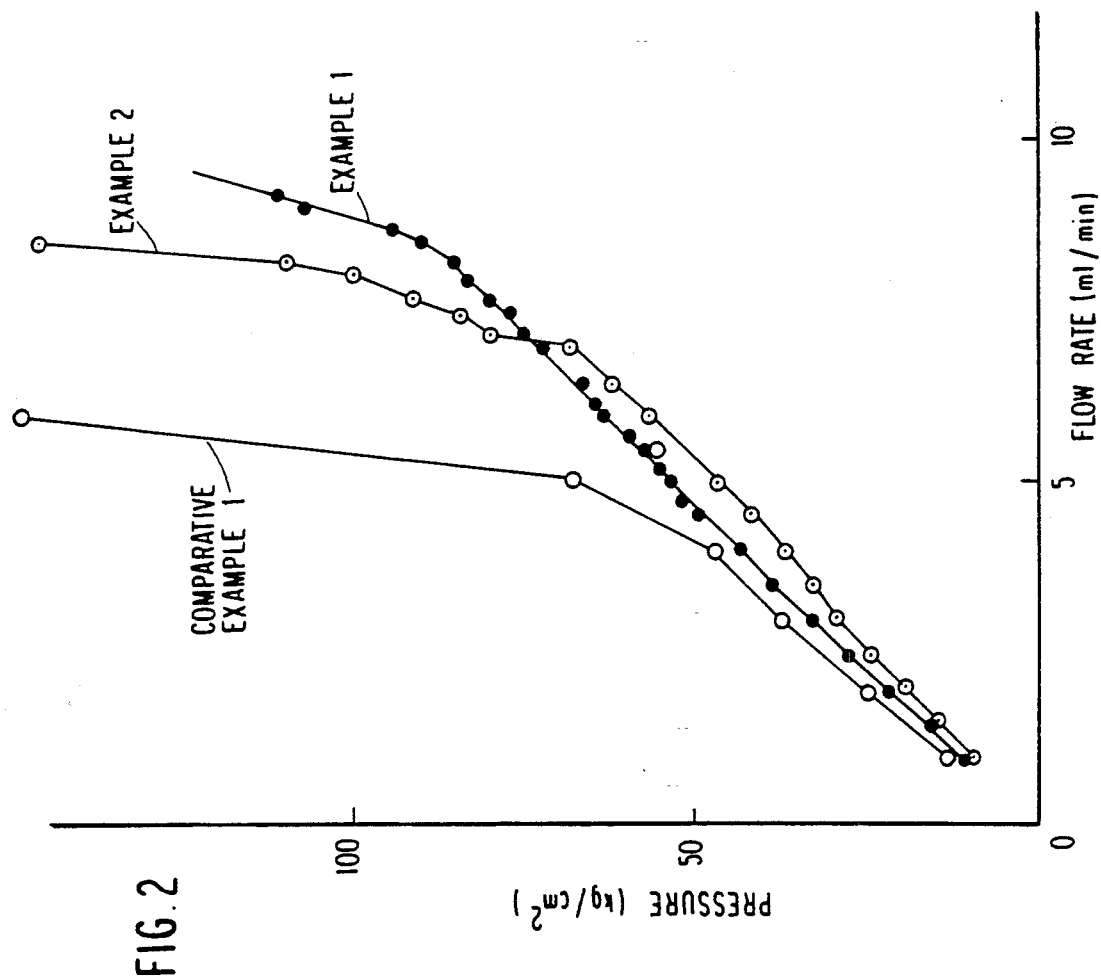
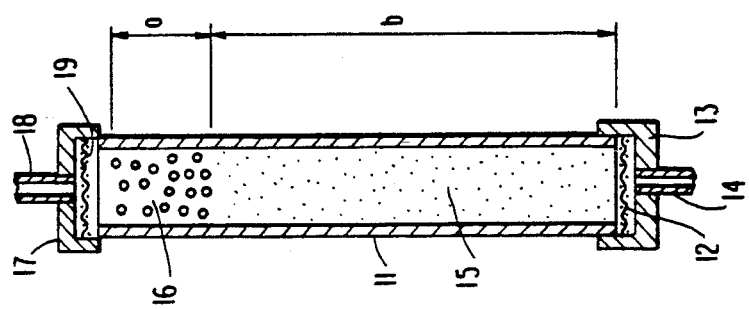

COLUMN FOR LIQUID CHROMATOGRAPHY

This is a continuation of application Ser. No. 07/449,399 filed Dec. 13, 1989 which is a continuation of application Ser. No. 07/246,368 filed Sep. 19, 1988, both now abandoned.

FIELD OF THE INVENTION

The present invention relates to a column for use in liquid chromatography which is packed with particles o a calcium phosphate based compound.

BACKGROUND OF THE INVENTION

Calcium phosphate based compounds, in particular hydroxyapatite, have excellent biocompatibility and find increasing use as implant materials including artificial tooth roots and bones. With a view to exploiting the high biocompatibility of calcium phosphate based compounds, attempts are also being made to use them as packings for liquid chromatography for separation of proteins, enzymes, etc.

The particles of calcium phosphate based compounds useful as packings for liquid chromatography can be produced by synthesizing a slurry of calcium phosphate by a wet method, spray drying the slurry to form particles, and firing the particles at a predetermined temperature. The lower the firing temperature, the higher the ability of the particles to adsorb proteins and other solutes but the lower the strength of the particles. On the other hand, if the firing temperature is increased, the adsorption capacity is lowered but the strength of the particles is improved.

A major problem with liquid chromatography columns that are packed with calcium phosphate based compounds is that when they are subjected to repeated use and the flow rate of the feed solution increases, a larger volume of voids form in the inlet portion of the column where the solvent stream is injected, thereby causing deterioration of the column performance. Two possible causes of this phenomenon are (1) dissolution of calcium ions into the solvent, and (2) mechanical impact caused by the supply of feed solutions. Because of these reasons, a column packed with particles of a calcium phosphate based compound that have been fired at a low temperature lacks durability in spite of its high capacity for adsorbing proteins and other solutes. On the other hand, a column packed with particles of a calcium phosphate based compound that has been fired at a high temperature suffers the problem of reduced adsorption capacity in spite of high durability.

SUMMARY OF THE INVENTION

An object, therefore, of the present invention is to provide a column for liquid chromatography that is packed with a particulate calcium phosphate based compound and which satisfies both requirements for high durability and good adsorption of solutes, such as proteins.

Other objects and effects of the present invention will be apparent from the following description.

In the course of the efforts to attain the above-stated object, the present inventors found that the action of the solvent to dissolve the packing and the mechanical impact by the solvent are most pronounced on the side where the solvent is injected into the column. As a result of continued studies, the present inventors found that the durability of the column could be improved without sacrificing its adsorption capacity by packing it with durable particles in the portion where the solvent is to be injected while particles having high adsorption capacity are packed in the remaining portion of the column. The present invention has been accomplished on the basis of this finding.

Therefore, the present invention generally relates to a column for liquid chromatography comprising particles of a calcium phosphate based compound packed in a column, wherein particles of a calcium phosphate based compound which are packed in the portion of said column where a solvent is to be injected have a durability higher than that of particles of a calcium phosphate compound which are packed in the remaining portion of said column.

BRIEF DESCRIPTION OF THE DRAWINGS

FIG. 1 is a diagrammatic cross section of a liquid chromatography column according to one embodiment of the present invention;

FIG. 2 is a graph showing the relationship between the flow rate and the pressure profiles obtained when distilled water was fed through the liquid chromatography columns constructed in Examples 1 and 2 and Comparative Example 1;

DETAILED DESCRIPTION OF THE INVENTION

Figure 3:
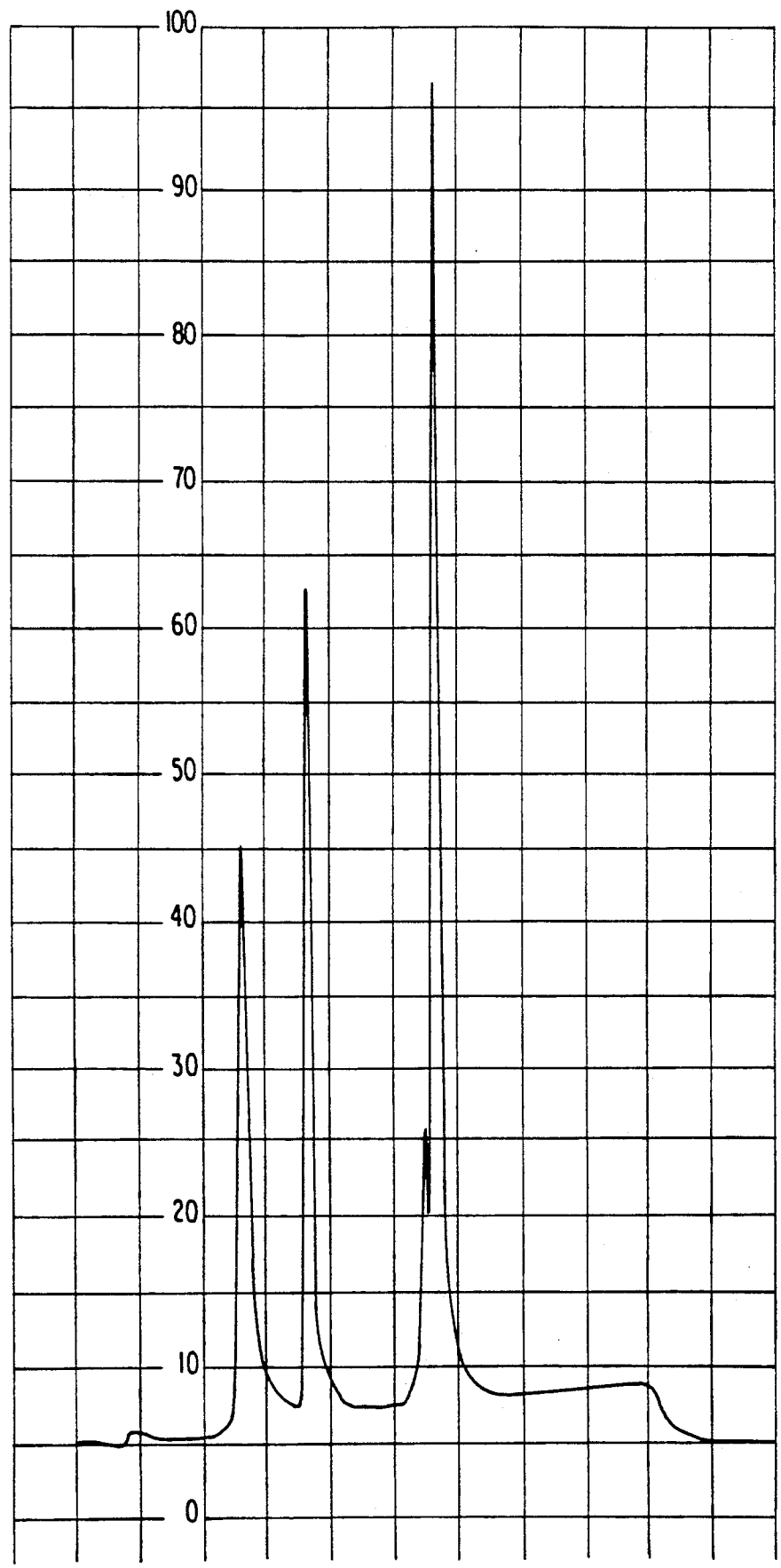
FIG. 3 is a pattern of chromatogram obtained in Example 3.

In the column of the present invention, particles of a calcium phosphate based compound that have been fired at a high temperature and which are packed in the portion where the solvent is to be injected serve as a sufficient buffer against not only the dissolving action but, also, the mechanical impact of the solvent so as to improve the durability of the packing in the column. On the other hand, the capacity of the column for adsorbing solutes, such as proteins, is retained at high level since the portion of the column other than where the solvent is to be injected is packed with particles of a calcium phosphate based compound which have been fired at a lower temperature.

Examples of the calcium phosphate based compound that can be used in the present invention include hydroxyapatite, tricalcium phosphate and fluoroapatite. Among these, hydroxyapatite is preferably used as the principal component since it has a particularly high capacity for adsorbing proteins and other solutes. The calcium phosphate based compounds listed above can be synthesized by a variety of known wet and dry processes.

The wet process is described, e.g., in Wallaeys, R.,. *Ann. Chim. (Paris)*, vol. 7, 808 and 823 (1952); Moreno, E. C., Gregory, T. M., Brown, W. E., *J. Res. Nat. Bur. Stand.*, vol. 72A, 773 (1968); and L. C. Bell, H. Mika, B. J. Kruger, *Archs. Oral. Biol.*, vol. 23, 329 to 336 (1978). The dry process is described, e.g., in Quinaux, N., *Arch. Intern. Physiol. Biochim.*, vol. 72, 337 (1964) and *Chem. Abstr.*, vol. 60, 15418a (1964); and Liteanu, C., Macarouci, D., *Studii Cercetari Chim.*, vol. 13, 157 (1962).

The particles of a calcium phosphate based compound may be prepared by spray-drying a slurry of calcium phosphate compound and then firing the resulting granules. Needless to say, this is not the only granulation method that can be employed. That is, the intended particles of a calcium phosphate based compound can be prepared by other method. It is more preferable for the particle size to be adjusted to be within a predetermined range by a certain means such as sieving. For instance, although this is a rough classification, particles having a particle size of 10 to 50 μm are used for separation and particles having a particle size of 1 to 10 μm a used for analysis.

It is necessary for the present invention to employ at least two kinds of particles of a calcium phosphate compound that have been fired at different temperatures, i.e., to pack the solvent inlet side of the column with particles that have been fired at the higher temperature and to pack the remaining portion of the column with particles that have been fired at the lower temperature.

Preferably, the solvent inlet side of the column is packed with particles that have been fired at about 850° C. or higher, preferably 900 to 1,200° C., and the remaining portion of the column is packed with particles that have been merely dried or have been fired at about 800° C. or lower, preferably 700° C. or lower. The strength of particles and their ability to adsorb solutes such as proteins have a tendency to change greatly at firing temperatures in the neighborhood of 800 to 850° C., and the intended effect of the present invention can be attained more efficiently by combining the two kinds of particles that have been fired in the temperature ranges set forth above.

The particles of a calcium phosphate based compound packed in the column may be composed of the same material throughout the column or they may be composed of different materials. For instance, the packing may be solely composed of hydroxyapatite particles that have been fired at two different temperatures. Alternatively, the solvent injection side of the column may be packed with fluoroapatite particles that have been fired at the higher temperature while the remaining portion of the column is packed with hydroxyapatite particles that have been fired at the lower temperature. Fluoroapatite is highly resistant to dissolution, so the durability of the column can be further improved by packing fluoroapatite particles in the portion where the solvent is to be injected.

The particles that have been fired at the higher temperature are preferably packed in that portion of the column which extends from the end of the solvent injection side to not more than one half, preferably not more than one tenth, the column length. Even if a longer area of the column is packed with these particles, there is not commensurate improvement in the durability of the column; to the contrary, the adsorption capacity of the column will drop considerably.

The particles of a calcium phosphate based compound used a column packing in the present invention may have a variety of sizes depending upon the specific use of the column. The particles having a particle size of 1 to 5 μm tend to increase a back pressure when a solvent is flown, and are particularly preferred in the present invention. The shape of the particles is also unlimited and may be spherical, amorphous, or any other form. They may even be porous.

FIG. 1 shown schematically a liquid chromatography column according to an embodiment of the present invention. As shown, a cylindrical column 11 is equipped with a filter 12 at the lower end. The exterior of the filter 12 is sealed with a cap 13 which is fitted with a solvent discharge pipe 14. The lower portion of the column 11 is packed over length b with particles 15 of a calcium phosphate based compound that have been fired at low temperature, and the upper portion of the column is packed over length a with particles 16 of a calcium phosphate based compound that have been fired at a higher temperature. The top end of the column 11 is equipped with a filter 19 and the exterior of the filter 19 is sealed with a cap 17 which is fitted with a solvent injection pipe 18.

When a solution of the sample to be analyzed is fed into the column through the solvent injection pipe 18, the components of the same are specifically adsorbed on particles 16 and 15 and flow through the column at different rates. Therefore, the sample can be separated into its respective components by successively recovering the effluents through the solvent discharge pipe 14. In the column shown in FIG. 1, particles 16 which have been fired at the higher temperature are packed in the portion of the column that extends downward of the solvent injection side by a length of a. As a result, these strong particles 16 provide a buffering action against the dissolving effect and mechanical impact of the solvent injected. Thus, the overall durability of the column is improved even though the particles 15 which have been fired at the lower temperature are packed in the downstream portion of the column over a length of b. Since these particles 15 have a satisfactory adsorption capacity, the column retains good separating characteristics.

The following examples are provided for the purpose of further illustrating the present invention but are in no way to be taken as limiting.

EXAMPLE 1

A slurry of hydroxyapatite was synthesized by a known wet process. The slurry was spray dried at 120° C. to form a powder comprising particles having an average size of 10 μm. This powder is designated powder A. Part of powder A was fired at 1,200° C. to make powder B.

A stainless steel column (7.5 mm in diameter and 100 mm in length) was packed with powder A by a wet method to cover the lower part of the column over a length of 7 cm. Thereafter, the head space on the solvent injection side of the column was packed with powder B by a wet method to cover the area over a length of 3 cm.

The thus constructed column for liquid chromatography was supplied with distilled water from the solvent feed end and the relationship between the flow rate and the pressure profile of this column was determined. The results are shown in FIG. 2.

EXAMPLE 2

A slurry of fluoroapatite was synthesized by a known process. This slurry was processed and fired at 1,200° C. as in the preparation of powder B in Example 1. The resulting powder was designated powder C.

A stainless steel column having the same dimensions as those adopted in Example 1 was packed with powder A as in Example 1 to cover the lower part of the column over a length of 9 cm. Thereafter, the head space on the solvent injection side of the column was packed with powder C to cover the area over a length of 1 cm.

The thus constructed column for liquid chromatography was supplied with distilled water from the solvent feed end and the relationship between the flow rate and the pressure profile of this column was determined. The results are shown in FIG. 2.

COMPARATIVE EXAMPLE 1

Powder A prepared in Example 1 was packed in the entire portion of a stainless steel column having the same dimensions as those adopted in Example 1.

The thus constructed column for liquid chromatography was supplied with distilled water from the solvent feed end and the relationship between the flow rate and the pressure profile of this column was determined. The results are shown in FIG. 2.

If the packing in the column retains its own shape, the pressure in the column will increase in proportion to the flow rate of feed solution. Therefore, the linear portion of each of the three curves in FIG. 2 represents the small occurrence of destruction or dissolution of the packing. On the other hand, the portion where the pressure increases exponentially signifies that the processing ability of the column is reduced on account of extensive destruction or dissolution of the packing.

The curves showing the results of Examples 1 and 2 have a linear portion that extends to a point where the flow rate is appreciably high. On the other hand, the curve showing the results of the Comparative Example 1 shifts to a region where the pressure increases exponentially at a much smaller flow rate.

As described on the foregoing, the liquid chromatography column of the present invention is packed in the solvent injection portion with the particles of a calcium phosphate based compound that have been fired at high temperature and the remaining portion of the column is packed with particles of a calcium phosphate based compound that have been fired at a lower temperature. Because of the combination of at least two different types of particles of a calcium phosphate based compound, the packing in the column has improved durability against the dissolving action and mechanical impact of solvents, yet it retains a satisfactory capacity for adsorbing solutes such as proteins.

EXAMPLE 3

A slurry of hydroxyapatite was synthesized by a known wet process. The slurry was spray dried at 120° C. to form a powder comprising particles having an average size of 10 μm. The powder has been heat treated at 800° C. This powder is designated powder C. Part of powder C was heat treated at 950° C. to make powder D.

A stainless steel column (7.5 mm in diameter and 100 mm in length) was packed with powder C by a wet method to cover the lower part of the column over a length of 7.5 cm. Thereafter, the head space on the solvent injection side of the column was packed with powder D by a wet method to cover the area over a length of 0.5 cm. The chromatogram pattern of the column thus prepared was obtained under the following conditions, and is shown in FIG. 3.

| Sample: | BSA | 10 μg/μl |
| --- | --- | --- |
| | Lysozyme | 1.2 μg/μl |
| | Cytochrome C | oxydized 5 μg/μl reduced |
| Amount injected: | 13 μl | |
| Solvent for measurement: | Sodium phosphate buffer pH 6.8 10–400 mM 30 min. linear gradient | |
| Chart speed: | 2.5 mm/min. | |

COMPARATIVE EXAMPLE 2

The powder C obtained in Example 3 above was packed in the same type of the column as used in Example 3 over the entire length of the column, and the chromatogram pattern was obtained under the same conditions as in Example 3.

Figure 4:
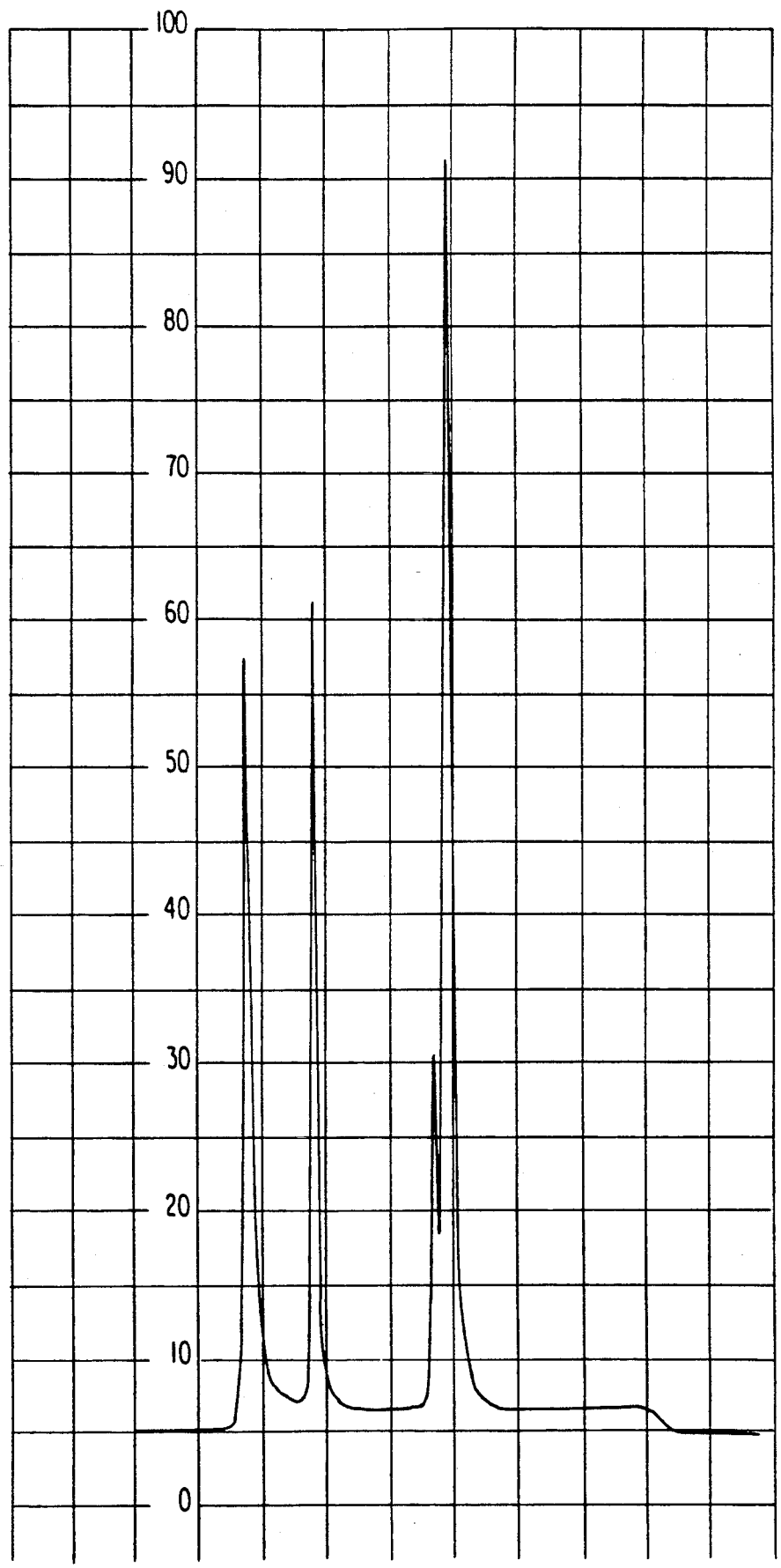
FIG. 4 is a pattern of chromatogram obtained in Comparative Example 2.

The pattern obtained is shown in FIG. 4.

While the invention has been described in detail and with reference to specific examples thereof, it will be apparent to one skilled in the art that various changes and modifications can be made therein without departing from the spirit and scope thereof.

What is claimed is:

1. A column for liquid chromatography comprising particles of a calcium phosphate based compound packed in a column, wherein particles of a calcium phosphate based compound which are packed in a portion of said column where a solvent is to be injected have a durability higher than that of particles of a calcium phosphate based compound which are packed in the remaining portion of said column and wherein said particles of a calcium phosphate based compound having a higher durability form an interfere with said particles of a calcium phosphate based compound in the remaining portion of said column.

2. A column for liquid chromatography as claimed in claim 1, wherein said particles of a calcium phosphate based compound packed in the portion of the column where a solvent is to be injected are particles which have been heat treated at a temperature higher than that of the particles of a calcium phosphate based compound packed in the remaining portion of the column.

3. A column for liquid chromatography as claimed in claim 2, wherein said particles packed in the portion of the column where a solvent is to be injected are particles fired at a temperature of 800° C. or higher.

4. A column for liquid chromatography as claimed in claim 2, wherein said particles packed in the portion of the column where a solvent is to be injected are packed in the portion of the column which extends from the end of the solvent injection side to not more than one half the column length.

5. A column for liquid chromatography as claimed in claim 1, wherein said particles of a calcium phosphate based compound consist of a hydroxyapatite.

6. A column for liquid chromatography as claimed in claim 1, wherein said particles of a calcium phosphate base compound packed in the portion of the column where a solvent is to be injected comprise a fluoroapatite, and said particles of a calcium phosphate based compound packed in the remaining portion of the column comprise a hydroxyapatite.

* * * * *